(12) United States Patent
Champagne et al.

(10) Patent No.: US 11,147,604 B2
(45) Date of Patent: Oct. 19, 2021

(54) BONE STABILIZATION DEVICE

(71) Applicant: Exsomed Holding Company, LLC, Phoenix, AZ (US)

(72) Inventors: Lloyd P. Champagne, Phoenix, AZ (US); Jozef Zoldos, Phoenix, AZ (US)

(73) Assignee: ExsoMed Corporation, Aliso Viejo, CA (US)

( * ) Notice: Subject to any disclaimer, the term of this patent is extended or adjusted under 35 U.S.C. 154(b) by 262 days.

(21) Appl. No.: 14/993,972

(22) Filed: Jan. 12, 2016

(65) Prior Publication Data

US 2017/0196609 A1 Jul. 13, 2017

(51) Int. Cl.
*A61B 17/86* (2006.01)
*A61B 17/88* (2006.01)

(52) U.S. Cl.
CPC ........ *A61B 17/8645* (2013.01); *A61B 17/864* (2013.01); *A61B 17/8615* (2013.01); *A61B 17/8635* (2013.01); *A61B 17/8897* (2013.01)

(58) Field of Classification Search
CPC .............. A61B 17/8625; A61B 17/863; A61B 17/8635; A61B 17/864; A61B 17/8645; A61B 17/72; A61B 17/7291
See application file for complete search history.

(56) References Cited

U.S. PATENT DOCUMENTS

| | | |
|---|---|---|
| 1,741,279 A | 12/1929 | Bowman |
| 2,037,586 A | 4/1936 | Olson |
| 2,210,455 A | 8/1940 | Hosking |
| 2,217,951 A | 10/1940 | Hosking |
| 2,229,892 A | 1/1941 | Hosking |
| 2,242,003 A | 5/1941 | Lorenzo |
| 3,078,900 A | 2/1963 | Walker |
| 3,275,055 A | 9/1966 | Gutshall |
| 3,397,699 A | 8/1968 | Kohl |
| 3,717,146 A | 2/1973 | Halloran |
| 4,016,874 A | 4/1977 | Maffei |
| 4,175,555 A | 11/1979 | Herbert |
| 4,350,465 A | 9/1982 | Lovisek |
| 4,380,414 A | 4/1983 | Capuano |

(Continued)

FOREIGN PATENT DOCUMENTS

| | | |
|---|---|---|
| CH | 643131 | 5/1984 |
| CH | 646858 | 12/1984 |

(Continued)

OTHER PUBLICATIONS

Machine English translation of DE 202013101135.*

(Continued)

*Primary Examiner* — Amy R Sipp
(74) *Attorney, Agent, or Firm* — Knobbe, Martens, Olson & Bear, LLP (57) ABSTRACT

A device and method for stabilizing a broken bone while it heals is disclosed. The device preferably has a (a) first (or proximal) section with a driving head, threads and a first diameter, and (b) second (or distal) section that is threaded and has a second diameter. The first section is preferably greater in diameter than the second section so that greater torque can be applied to tighten the device. The device may include one or more self-tapping structures to lessen the torque required to screw it into a bone.

18 Claims, 7 Drawing Sheets

(56) References Cited

U.S. PATENT DOCUMENTS

| | | |
|---|---|---|
| 4,463,753 A | 8/1984 | Gustilo |
| 4,471,777 A | 9/1984 | McCorkle |
| 4,584,722 A | 4/1986 | Levy et al. |
| 4,608,965 A | 9/1986 | Anspach |
| 4,764,066 A | 8/1988 | Terrell |
| 4,781,191 A | 11/1988 | Thompson |
| 4,812,095 A | 3/1989 | Piacenti |
| 4,820,235 A | 4/1989 | Weber et al. |
| 4,842,463 A | 6/1989 | Landt |
| 4,901,717 A | 2/1990 | Moore et al. |
| 4,909,789 A | 3/1990 | Taguchi et al. |
| 4,950,270 A | 8/1990 | Bowman et al. |
| 5,061,283 A | 10/1991 | Silvestrini |
| 5,234,299 A | 8/1993 | Giannuzzi |
| 5,312,255 A | 5/1994 | Bauer |
| 5,345,927 A | 9/1994 | Bonutti |
| 5,443,466 A | 8/1995 | Shah |
| 5,522,846 A | 6/1996 | Bonutti |
| 5,645,545 A | 7/1997 | Bryant |
| 5,667,510 A | 9/1997 | Combs |
| 5,690,633 A | 11/1997 | Taylor et al. |
| 5,840,078 A | 11/1998 | Yerys |
| 5,853,413 A | 12/1998 | Carter et al. |
| 6,030,162 A * | 2/2000 | Huebner ............ A61B 17/1682 411/263 |
| 6,187,007 B1 | 2/2001 | Frigg |
| 6,221,006 B1 | 4/2001 | Dubrul et al. |
| 6,231,319 B1 | 5/2001 | Iida et al. |
| 6,231,413 B1 | 5/2001 | Tsukamoto |
| 6,306,140 B1 | 10/2001 | Siddiqui |
| 6,394,725 B1 | 5/2002 | Dicke |
| 6,475,242 B1 | 11/2002 | Bramlet |
| 6,517,541 B1 * | 2/2003 | Sesic ..................... A61B 17/72 606/62 |
| 6,592,623 B1 | 7/2003 | Bowlin et al. |
| 6,607,530 B1 | 8/2003 | Carl et al. |
| 6,808,526 B1 | 10/2004 | Magerl et al. |
| 7,037,309 B2 | 5/2006 | Well et al. |
| 7,041,106 B1 | 5/2006 | Carver et al. |
| 7,063,491 B2 | 6/2006 | French |
| 7,334,976 B2 | 2/2008 | Dicke |
| 7,465,135 B2 | 12/2008 | Fritsch |
| 7,507,242 B2 | 3/2009 | Triplett et al. |
| 7,604,659 B2 | 10/2009 | Lee |
| 7,708,738 B2 | 5/2010 | Fourcault et al. |
| 7,766,942 B2 | 8/2010 | Patterson |
| 7,988,724 B2 | 8/2011 | Salahieh et al. |
| 8,011,866 B2 | 9/2011 | Harris |
| 8,157,803 B1 | 4/2012 | Zirkle, Jr. |
| 8,348,575 B2 | 1/2013 | Walther |
| 8,398,687 B2 | 3/2013 | Vasta et al. |
| 8,414,648 B2 | 4/2013 | Reiley |
| 8,419,776 B2 | 4/2013 | Prandi et al. |
| 8,518,042 B2 | 8/2013 | Winsow et al. |
| 8,568,462 B2 | 10/2013 | Sixto et al. |
| 8,597,337 B2 | 12/2013 | Champagne |
| 8,608,783 B2 | 12/2013 | Graham et al. |
| 8,814,918 B2 | 8/2014 | Orbay et al. |
| 8,852,253 B2 | 10/2014 | Mafi |
| 8,864,804 B2 | 10/2014 | Champagne et al. |
| 8,888,429 B2 | 11/2014 | Pamer |
| 8,906,075 B2 | 12/2014 | Conley et al. |
| 9,017,404 B2 | 4/2015 | Champagne et al. |
| 9,046,120 B2 | 6/2015 | Phua |
| 9,086,088 B2 | 7/2015 | Walther |
| 9,175,715 B2 | 11/2015 | Babej |
| 9,265,600 B2 | 2/2016 | Niese |
| 9,480,515 B2 | 11/2016 | Champagne |
| 9,539,084 B2 | 1/2017 | Champagne |
| 10,098,680 B2 | 10/2018 | Champagne |
| 2001/0049529 A1 | 12/2001 | Cachia et al. |
| 2002/0045897 A1 | 4/2002 | Dixon et al. |
| 2002/0055747 A1 | 5/2002 | Cano et al. |
| 2002/0055749 A1 | 5/2002 | Esnouf et al. |
| 2002/0143337 A1 | 10/2002 | Orbay et al. |
| 2002/0198527 A1 | 12/2002 | Muckter |
| 2003/0014077 A1 | 1/2003 | Leung |
| 2003/0028193 A1 * | 2/2003 | Weil ..................... A61B 17/863 606/304 |
| 2003/0083661 A1 | 5/2003 | Orbay et al. |
| 2003/0130735 A1 * | 7/2003 | Rogalski ............... A61F 2/0811 623/13.15 |
| 2004/0193217 A1 | 9/2004 | Lubbers |
| 2004/0210227 A1 | 10/2004 | Trail et al. |
| 2004/0260288 A1 | 12/2004 | Means |
| 2004/0260291 A1 * | 12/2004 | Jensen ............... A61B 17/1728 606/915 |
| 2005/0075642 A1 | 4/2005 | Felt et al. |
| 2005/0085824 A1 | 4/2005 | Castaneda |
| 2005/0107791 A1 | 5/2005 | Manderson |
| 2005/0143735 A1 | 6/2005 | Kyle |
| 2006/0129153 A1 | 6/2006 | Klaue et al. |
| 2006/0149249 A1 | 7/2006 | Mathoulin et al. |
| 2006/0165506 A1 | 7/2006 | Panasik |
| 2006/0195099 A1 | 8/2006 | Bottlang |
| 2006/0271061 A1 | 11/2006 | Beyar |
| 2006/0276790 A1 | 12/2006 | Dawson |
| 2007/0027547 A1 | 2/2007 | Rydell et al. |
| 2007/0135816 A1 | 6/2007 | Kropf et al. |
| 2007/0282342 A1 | 12/2007 | Niederberger et al. |
| 2007/0299449 A1 | 12/2007 | Allinniemi et al. |
| 2008/0183220 A1 | 7/2008 | Glazer |
| 2008/0219801 A1 | 9/2008 | Toenjes |
| 2008/0249547 A1 | 10/2008 | Dunn |
| 2008/0249574 A1 | 10/2008 | McCombs et al. |
| 2009/0062868 A1 | 3/2009 | Casutt |
| 2009/0299369 A1 | 12/2009 | Orbay et al. |
| 2010/0069970 A1 | 3/2010 | Lewis et al. |
| 2010/0106254 A1 | 4/2010 | Delsignore |
| 2010/0121136 A1 | 5/2010 | Champagne |
| 2010/0130978 A1 | 5/2010 | Orbay et al. |
| 2010/0211115 A1 | 8/2010 | Tyber et al. |
| 2010/0278614 A1 | 11/2010 | Bickford |
| 2010/0312286 A1 | 12/2010 | Dell'Oca |
| 2010/0324556 A1 | 12/2010 | Tyber et al. |
| 2011/0009865 A1 | 1/2011 | Orfaly |
| 2011/0130794 A1 | 6/2011 | Vaidya |
| 2011/0293387 A1 * | 12/2011 | Chang .................. F16B 25/103 411/387.1 |
| 2012/0083847 A1 | 4/2012 | Heubner et al. |
| 2012/0136398 A1 * | 5/2012 | Mobasser ............ A61B 17/863 606/311 |
| 2012/0191140 A1 | 7/2012 | Bonutti |
| 2012/0221104 A1 | 8/2012 | Altman et al. |
| 2012/0253464 A1 | 10/2012 | Hwang et al. |
| 2012/0253465 A1 | 10/2012 | Missos |
| 2013/0012987 A1 | 1/2013 | Klein et al. |
| 2013/0053961 A1 | 2/2013 | Darwin et al. |
| 2013/0060333 A1 | 3/2013 | Gonzalez |
| 2013/0131699 A1 | 5/2013 | Jiango et al. |
| 2013/0138123 A1 | 5/2013 | Stone et al. |
| 2013/0165979 A1 | 6/2013 | Greenberg et al. |
| 2013/0190872 A1 | 7/2013 | Makower et al. |
| 2013/0197592 A1 | 8/2013 | Mafi |
| 2013/0245626 A1 | 9/2013 | Lavi et al. |
| 2013/0245700 A1 | 9/2013 | Choinski |
| 2013/0245762 A1 | 9/2013 | Van Kampen et al. |
| 2013/0261662 A1 | 10/2013 | Mayer et al. |
| 2013/0274879 A1 | 10/2013 | Champagne et al. |
| 2013/0282058 A1 | 10/2013 | ElAttrache et al. |
| 2013/0325011 A1 | 12/2013 | Cleveland et al. |
| 2014/0025124 A1 * | 1/2014 | Champagne ......... A61B 17/863 606/308 |
| 2014/0067063 A1 | 3/2014 | Bonutti |
| 2014/0257349 A1 | 9/2014 | Sudekum |
| 2014/0276846 A1 | 9/2014 | Mauldin |
| 2014/0277191 A1 * | 9/2014 | Evans ................ A61B 17/7225 606/308 |
| 2014/0336712 A1 | 11/2014 | Strnad et al. |
| 2015/0066060 A1 | 3/2015 | Bojarski |
| 2015/0088136 A1 | 3/2015 | Kotuljac et al. |
| 2015/0094722 A1 | 4/2015 | Champagne et al. |
| 2015/0094724 A1 | 4/2015 | Champagne et al. |
| 2015/0094777 A1 | 4/2015 | Champagne et al. |

(56) References Cited

U.S. PATENT DOCUMENTS

| | | | |
|---|---|---|---|
| 2015/0173737 A1 | 6/2015 | Champagne et al. | |
| 2015/0182325 A1 | 7/2015 | Champagne et al. | |
| 2015/0201984 A1 | 7/2015 | Orbay et al. | |
| 2016/0030097 A1* | 2/2016 | Mildner | A61B 17/863 606/304 |
| 2016/0256290 A1 | 9/2016 | Seavey et al. | |
| 2016/0296263 A1 | 10/2016 | Champagne et al. | |
| 2016/0296264 A1 | 10/2016 | Champagne et al. | |
| 2016/0338748 A1 | 11/2016 | Champagne et al. | |
| 2017/0014170 A1* | 1/2017 | Fallin | A61B 17/7291 |
| 2017/0027577 A1 | 2/2017 | Kubiak et al. | |
| 2017/0035553 A1 | 2/2017 | Champagne et al. | |
| 2017/0049167 A1 | 2/2017 | Champagne et al. | |
| 2017/0189090 A1 | 7/2017 | Champagne et al. | |
| 2017/0325827 A1 | 11/2017 | Champagne et al. | |
| 2018/0021124 A1 | 1/2018 | Champagne et al. | |
| 2020/0237415 A1 | 7/2020 | Champagne et al. | |

FOREIGN PATENT DOCUMENTS

| | | | |
|---|---|---|---|
| CH | 202013101135 U1 * | 6/2014 | A61B 17/863 |
| DE | 2713386 | 11/1978 | |
| DE | 102007003645 | 7/2008 | |
| EP | 0597223 | 5/1994 | |
| EP | 1378205 | 1/2004 | |
| EP | 2606843 | 6/2013 | |
| EP | 2872073 | 9/2018 | |
| GB | 2007099 | 5/1979 | |
| GB | 2181356 | 4/1987 | |
| WO | WO199733537 | 9/1997 | |
| WO | WO2004093700 | 4/2004 | |
| WO | WO2005092226 | 10/2005 | |
| WO | WO2006105935 | 12/2006 | |
| WO | WO2007081601 | 7/2007 | |
| WO | WO2007109140 | 9/2007 | |
| WO | WO2008063156 | 5/2008 | |
| WO | WO2010151589 | 12/2010 | |
| WO | 2012050424 | 4/2012 | |
| WO | WO2014011933 | 1/2014 | |
| WO | 2014089522 | 6/2014 | |
| WO | 2015050900 | 4/2015 | |
| WO | WO2015050895 | 9/2015 | |
| WO | WO2015050896 | 9/2015 | |
| WO | WO2015050898 | 9/2015 | |
| WO | WO2015050902 | 9/2015 | |
| WO | 2016186847 | 11/2016 | |

OTHER PUBLICATIONS

PCT; International Search Report and Written Opinion dated Sep. 17, 2010 in Application No. PCT/US2009/046662.
EP; Examination Report dated May 30, 2011 in Application No. EP 09774002.1.
USPTO; Office Action dated Oct. 4, 2011 in U.S. Appl. No. 12/372,712.
USPTO; Office Action dated Mar. 21, 2012 in U.S. Appl. No. 12/480,676.
EP; Examination Report dated May 25, 2012 in Application No. EP 09774002.1.
USPTO; Office Action dated May 29, 2012 in U.S. Appl. No. 12/372,712.
USPTO; Office Action dated Sep. 18, 2012 in U.S. Appl. No. 12/480,676.
USPTO; Office Action dated Mar. 22, 2013 in U.S. Appl. No. 12/372,712.
USPTO; Notice of Allowance dated Jul. 30, 2013 in U.S. Appl. No. 12/372,712.
PCT; International Search Report and Written Opinion dated Sep. 9, 2013 in Application No. PCT/US2013/050155.
USPTO; Office Action dated Sep. 24, 2013 in U.S. Appl. No. 12/480,676.
USPTO; Office Action dated Feb. 18, 2014 in U.S. Appl. No. 13/555,933.
USPTO; Notice of Allowance dated Jun. 25, 2014 in U.S. Appl. No. 13/555,933.
USPTO; Office Action dated Aug. 29, 2014 in U.S. Appl. No. 13/648,019.
PCT; International Search Report and Written Opinion dated Dec. 10, 2014 in Application No. PCT/US2014/058463.
PCT; International Search Report and Written Opinion dated Dec. 12, 2014 in Application No. PCT/US2014/058474.
USPTO; Notice of Allowance dated Dec. 31, 2014 in U.S. Appl. No. 13/648,019.
PCT; International Search Report and Written Opinion dated Jan. 20, 2015 in Application No. PCT/US2014/058448.
PCT; International Search Report and Written Opinion dated Feb. 9, 2015 in Application No. PCT/US2014/058441.
USPTO; Office Action dated Dec. 9, 2015 in U.S. Appl. No. 14/640,657.
USPTO; Office Action dated Sep. 22, 2015 in U.S. Appl. No. 14/503,228.
USPTO; Office Action dated Oct. 5, 2015 in U.S. Appl. No. 13/940,173.
USPTO; Final Office Action dated May 2, 2016 in U.S. Appl. No. 14/503,228.
USPTO; Final Office Action dated May 23, 2016 in U.S. Appl. No. 14/640,657.
USPTO; Final Office Action dated May 23, 2016 in U.S. Appl. No. 13/940,173.
USPTO; Non-Final Office Action dated Nov. 4, 2016 in U.S. Appl. No. 14/503,119.
USPTO; Non-Final Office Action dated Jan. 27, 2017 in U.S. Appl. No. 14/503,157.
USPTO; Non-Final Office Action dated Feb. 9, 2017 in U.S. Appl. No. 14/503,228.
USPTO; Non-Final Office Action dated Apr. 10, 2017 in U.S. Appl. No. 14/641,024.
USPTO; Final Office Action dated Aug. 31, 2017 in U.S. Appl. No. 14/503,228.
USPTO; Notice of Allowance dated Jul. 1, 2016 in U.S. Appl. No. 13/940,173.
USPTO; Notice of Allowance dated Sep. 1, 2016 in U.S. Appl. No. 14/640,657.
USPTO; Final Office Action dated Jun. 2, 2017 in U.S. Appl. No. 14/503,157.
USPTO; Final Office Action dated Jun. 13, 2017 in U.S. Appl. No. 14/503,119.
PCT; International Search Report and Written Opinion dated Sep. 30, 2014 in Application No. PCT/US2014/058472.
PCT; International Search Report and Written Opinion dated May 4, 2016 in Application No. PCT/US2016/030850.
USPTO; Non-Final Office Action dated Nov. 1, 2017 in U.S. Appl. No. 15/297,698.
USPTO; Non-Final Office Action dated Nov. 28, 2017 in U.S. Appl. No. 15/189,845.
USPTO; Non-Final Office Action dated Nov. 30, 2017 in U.S. Appl. No. 15/189,829.
USPTO; Requirement for Restriction dated Nov. 30, 2017 in U.S. Appl. No. 15/214,412.
USPTO; Non-Final Office Action dated Dec. 8, 2017 in U.S. Appl. No. 15/146,824.
USPTO; Non-Final Office Action dated Dec. 15, 2017 in U.S. Appl. No. 14/984,145.
USPTO; Non-Final Office Action dated Feb. 21, 2018 in U.S. Appl. No. 15/151,252.
USPTO; Non-Final Office Action dated Feb. 27, 2018 in U.S. Appl. No. 14/503,157.
USPTO; Non-Final Office Action dated Mar. 5, 2018 in U.S. Appl. No. 15/214,412.
EP; Examination Report dated Feb. 12, 2016 in Application No. EP 13742332.3.
EP; 2nd Examination Report dated Oct. 11, 2016 in Application No. EP 13742332.3.

(56) References Cited

OTHER PUBLICATIONS

EP; Notice of Allowance dated Apr. 12, 2018 in Application No. EP 13742332.3.
USPTO; Non-Final Office Action dated Jun. 6, 2018 in U.S. Appl. No. 14/503,228.
USPTO; Notice of Allowance dated Jun. 15, 2018 in U.S. Appl. No. 15/189,845.
USPTO; Final Office Action dated Jun. 26, 2018 in U.S. Appl. No. 14/984,145.
USPTO; Notice of Allowance dated Jul. 11, 2018 in U.S. Appl. No. 15/189,845.
USPTO; Final Office Action dated Aug. 8, 2018 in U.S. Appl. No. 15/214,412.
USPTO; Final Office Action dated Aug. 13, 2018 in U.S. Appl. No. 15/151,252.
USPTO; Notice of Allowance dated Sep. 18, 2018 in U.S. Appl. No. 15/151,252.
USPTO; Final Office Action dated Oct. 17, 2018 in U.S. Appl. No. 15/146,824.
USPTO; Final Office Action dated Oct. 25, 2018 in U.S. Appl. No. 14/503,157.
USPTO; Notice of Allowance dated Nov. 9, 2018 in U.S. Appl. No. 15/151,252.
USPTO; Notice of Allowance dated Nov. 27, 2018 in U.S. Appl. No. 14/984,145.
USPTO; Non-Final Office Action dated Dec. 11, 2018 in U.S. Appl. No. 15/214,412.

\* cited by examiner

BONE STABILIZATION DEVICE

FIELD OF THE INVENTION

The present invention relates to a device implantable in a bone to stabilize it while it heals, and which is particularly suitable for use in a metacarpal bone.

BACKGROUND OF THE INVENTION

The palm of the hand is made up of bones called metacarpals, and a metacarpal connects each finger and thumb to the hand. Each finger and thumb is formed of bones called phalanges. The connection of the phalanges to the metacarpals is called a "knuckle" joint or metacarpophalangeal joint (MCP joint), and acts like a hinge when the fingers or thumb are bent. In the metacarpal bones, the proximal portion and mid metacarpal portion is relatively narrower, and the distal portion is relatively wider with respect to both the internal medullary canal and external diameter.

In each finger, there are three phalanges that are separated by two joints called the interphalangeal joints (IP joints). The proximal IP joint (PIP joint) is the one closest to the MCP joint. The other joint closest to the end of the finger is the distal IP joint (DIP joint). The thumb just has one IP joint. The joints are covered on the ends with articular cartilage Damage to the metacarpal bone may occur as a result of a sprain or fracture. Typically, once the metacarpal bone is lined up after an injury it must be stabilized in position while it heals.

To stabilize a broken metacarpal bone, it is now known to use a non-threaded, smooth metal shaft (hereafter "nail") positioned in the metacarpal bone to hold it in position while the bone heals. An opening is first formed in the metacarpal bone, wherein the opening extends through the fracture and the nail is positioned in the opening to provide lateral stability for the parts of the bone on either side of the fracture. After a certain period, a second surgery is required to remove the nail from the bone. Problems with the nail are that, because it is not anchored in the bone, it can migrate through the metacarpal bone and into surrounding tissue. Sometimes this can result in damage to soft tissue, such as a severed or damaged tendon or cartilage, and/or cause pain. Another problem with the nail is that, because it can migrate, a second surgery is required to remove it. Additionally, the proximal end of pins and nails can cause tendon irritation, tendon rupture or skin irritation and infection.

One potential solution to this problem is to insert a screw into the bone. Such a procedure could be lengthy, and there would be a possibility of bone damage, or damage to the driving head of the screw, which could prevent complete insertion of the screw into the bone, or breakage of the screw because the screw must be relatively long and slender. Current screws are not designed specifically for intramedullary placement. They are not long enough, and if a current screw design was simply lengthened, it would lack a shaft and driving portion sufficient to handle the torque required.

SUMMARY OF THE INVENTION

The present invention solves the problems associated with repairing a bone, such as a metacarpal bone, by providing a device that is a screw having a first (or proximal in relation to the screw) section and a second (or distal in relation to the screw) section. As used herein with respect to a device, or section of a device, according to the invention, "diameter" includes the diameter of the threads, unless otherwise specified. The first section preferably has a greater diameter than the second section, and the end (or tip) of the first section has a driving surface (or hand) to receive and be turned by an appropriate driving tool. The screw is inserted into the metacarpal in a retrograde fashion. In this manner, the smaller diameter second section can fit in the narrower proximal and mid portion of a bone, such as a metacarpal bone. The larger diameter first section fits into the larger, distal portion of the bone (such as a metacarpal head), and the driving head at the end of the first section is wider in order to accept a larger driving tool and generate more torque to drive the screw into position.

In preferred embodiments, the device has a cutting structure at the tip of the second end, and a second cutting structure between the first section and second section. The cutting structures (either one, two or more, if used) assist in placing the screw into the bone with less torque.

It is also preferred, but not required, that there is an immediate step from the thicker diameter of the first section to the thinner diameter of the second section, and that the second cutting structure be positioned immediately before, or be included as part of, the initial threads in the first section, and that the cutting structure be approximately the same diameter as the first section.

In one exemplary embodiment, the second section is completely threaded (which as used herein means substantially completely threaded) and has an overall outer diameter (including the threads) of 4 mm. The first section is also preferably completely threaded (which as used herein means substantially completely threaded) and has an overall outer diameter of 4.5 mm. The first section, however, may have a diameter of 3.0 mm-5.0 mm, and the second section may have a diameter of 3.0 mm-4.5 mm. It is preferred that the diameter of the first section be about 0.5 mm greater than the diameter of the second section. The first section may instead have a diameter that is 7%-15% greater than the diameter of the second section.

The threads most preferably run along the entire length (which means substantially the entire length) of the device. The threads may have the same pitch and height along the length of the device, or the threads on the first section may have a different pitch and/or height than the threads on the second section.

Because of the configuration of device according to the invention, the device may be inserted and retained in a bone such as the metacarpal. The device generates sufficient fixation to the bone, is thin enough to fit into the proximal and middle portions of the bone, and strong enough so that torque applied to it threads the device into the bone rather than causing the device to deform.

DETAILED DESCRIPTION OF PREFERRED EMBODIMENTS

Figure 1:
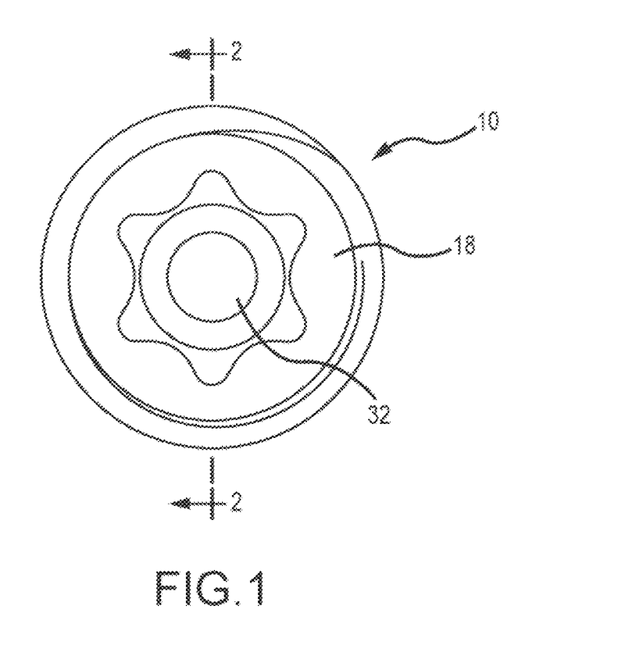
FIG. 1 is a top view of the head of one embodiment of a device according to the invention.
Figure 2:
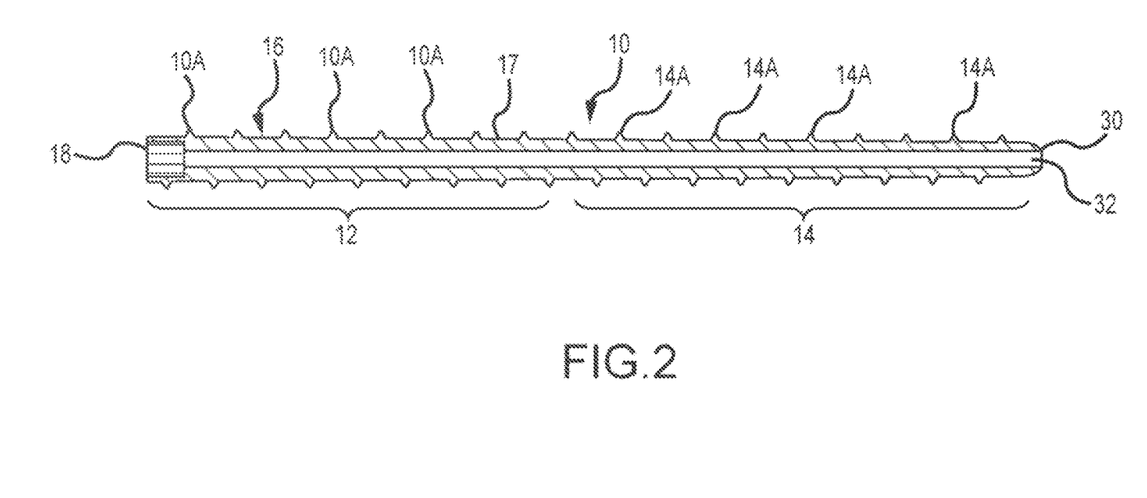
FIG. 2 is a cross-sectional side view of the device of FIG. 1.

Turning now to the figures, where the purpose is to describe preferred embodiments of the invention and not to limit same, FIG. 1 shows an exemplary embodiment 10 of the invention. Device 10 may be formed of any suitable material, such as titanium steel, stainless steel or nitinol. Device 10 has a first (or proximal) section 12, a second (or distal) section 14, and a shaft 16 with an outer surface 17. Device 10 may be between 3.5 cm and 8.5 cm or between 6.5 cm and 8 cm in length, or have a length of about 7 cm.

Figure 3:
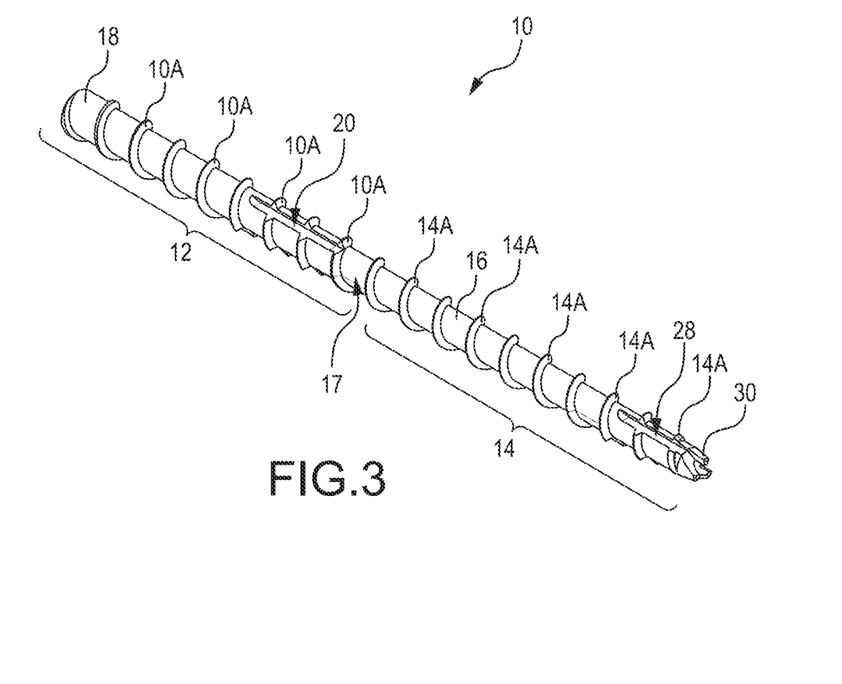
FIG. 3 is a perspective, side view of the device of FIGS. 1 and 2.
Figure 4:
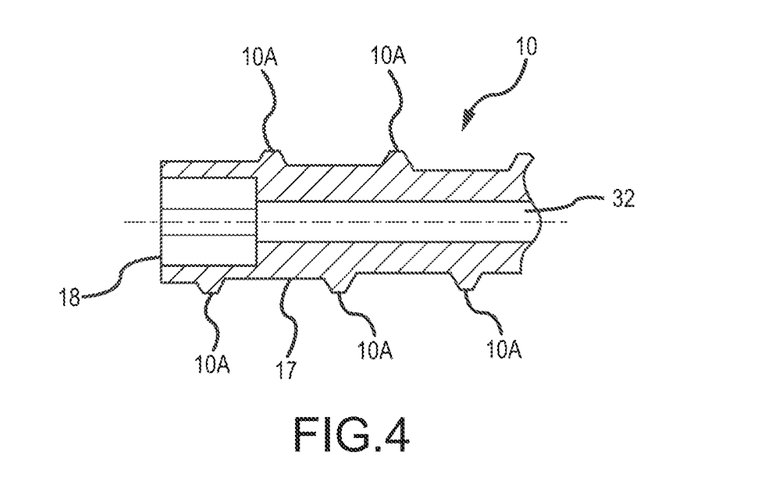
FIG. 4 is a partial, cross-sectional side view of the device of FIGS. 1-3.
Figure 5:
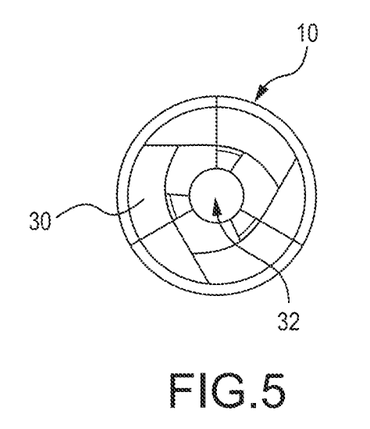
FIG. 5 is an end view of the device of FIGS. 1-4.
Figure 6:
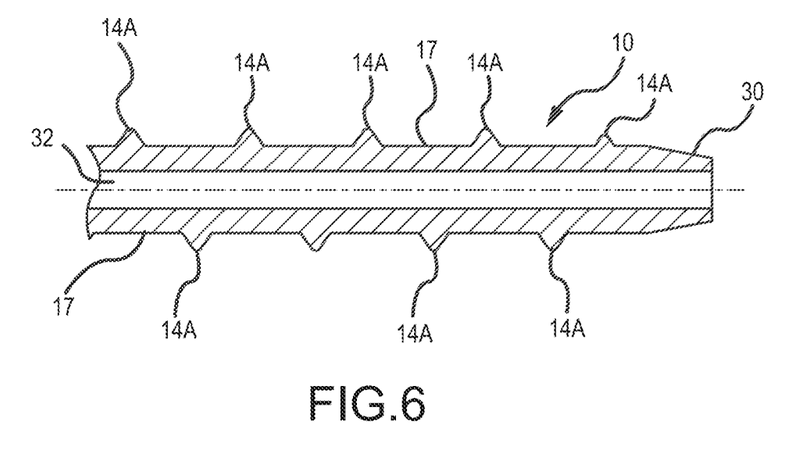
FIG. 6 is a partial, cross-sectional side view of the device of FIGS. 1-5.
Figure 9:
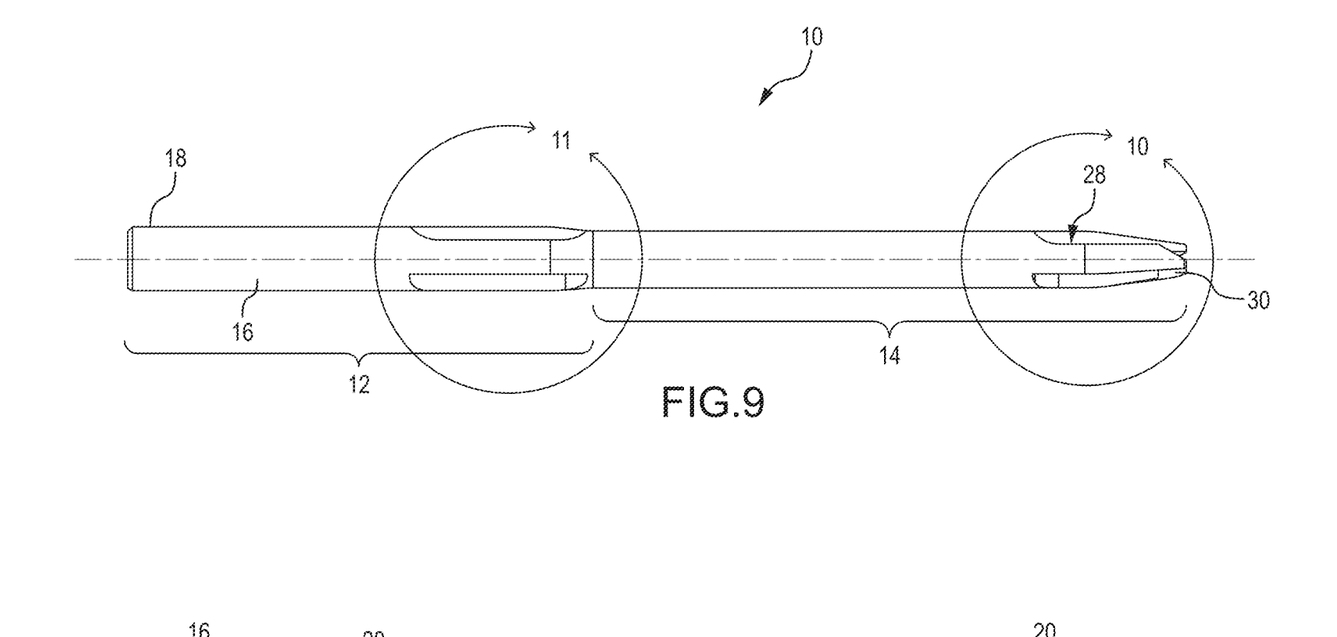
FIG. 9 illustrates a side view of the device of FIGS. 1-6 with a cutting flute shown without threads for clarity.
Figure 11:
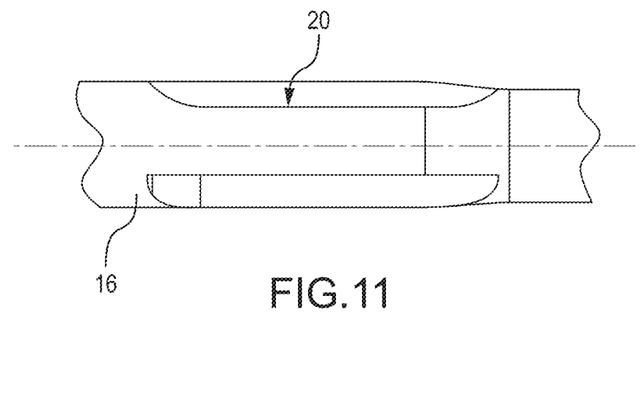
FIG. 11 illustrates a detailed view of a portion of the device of FIG. 9 with a proximal cutting flute shown without threads for clarity.

First section 12 has first threads 10A which preferably have a height of about 0.5 to 1 mm as measured from outer surface 17, and a pitch of about 1 mm per revolution. A driving surface, or head, 18 is shown as being the same diameter of first section 12, but head 18 may have a different diameter or be of a different shape, such as triangular. Head 18 may accept any suitable driver configuration, such as a Torx drive, slotted, Pozidriv, Robertson, tri-wing, Torq-Set, SpannerHead, Triple Square, and hex head. A cutting structure 20 is shown in FIGS. 3, 9, and 11 as positioned at the distal end of first section 12, and it preferably has the same height as threads 10A, or is formed in one or more threads 10A, and the portion of section 12 that includes cutting structure 20 as shown preferably has the same diameter as the rest of first section 12. The preferred configuration of cutting structure 20 is self-tapping features in one or more threads 10A, which are preferably indentations that basically make the thread serrated, as shown in FIG. 3. First section 12 preferably has a diameter of 3.0 mm to 5.0 mm, and most preferably about 4.5 mm. First section 12 preferably extends between about 25% to 45% of the length of device 10, and in one preferred embodiment is about 40% of the length.

Figure 10:
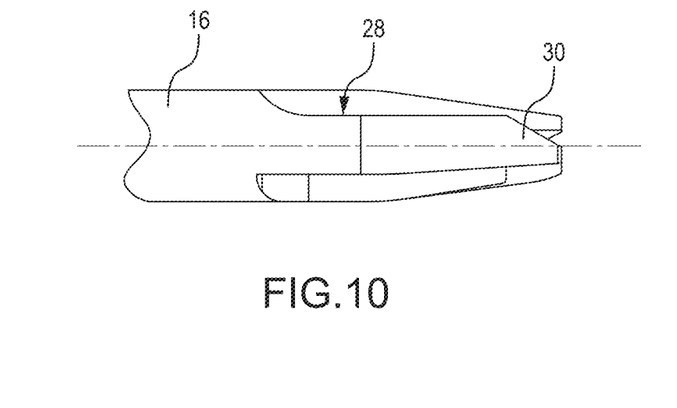
FIG. 10 illustrates a detailed view of a portion of the device of FIG. 9 with a distal cutting flute shown without threads for clarity.

Second section 14 has first threads 14A which preferably have a height of about 0.5-1 mm as measured from outer surface 17, and a pitch of about 1 mm/revolution. A cutting structure 28 is shown in FIGS. 3, 9, and 10 at the distal tip 30 of second section 12, which may be any known self-tapping feature. Second section 14 preferably has a diameter of 3.0 mm to 4.5 mm, most preferably about 4.0 mm, and most preferably about 0.5 mm less than the diameter of the first section. Second section 14 preferably extends between about 55% to 75% of the length of device 10, and in one preferred embodiment is about 60% of the length.

Threads 10A on the first section 10 preferably have the same pitch as the thread 14A, and extend outward from surface 17 of device 10 by the same amount as threads 14A, although any suitable thread configuration is acceptable, including threads with differential pitches threads on either or both of sections 12 and 14.

Device 10 may be cannulated or non-cannulated. As shown, device 10 has a cannula 32 extending therethrough. A non-cannulated device may be have a smaller diameter than a cannulated device.

The diameter of the first section is preferably about 4%, or 5%, or 4% to 7%, or 4% to 10%, of the length of device 10.

Figure 7:
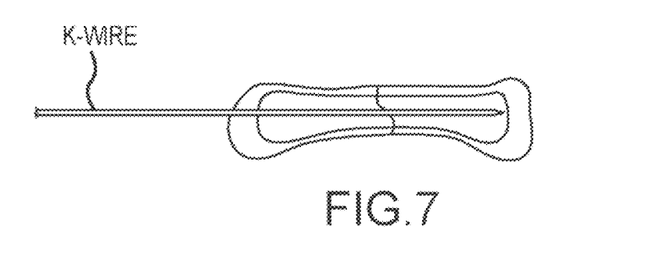
FIGS. 7-7B show one method for installing a device according to FIGS. 1-6 into a metacarpal bone.
Figure 7A:
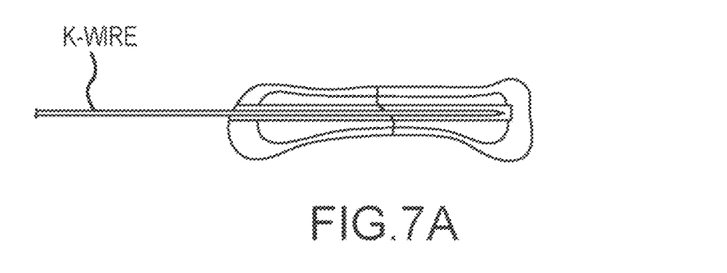
Figure 7B:
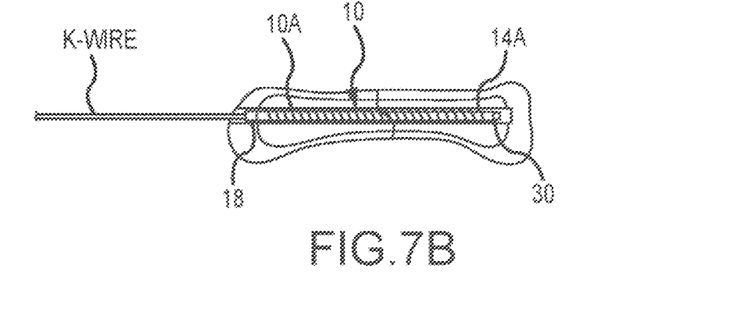

FIGS. 7-7B depict a method for installing device 10 into a fractured metacarpal bone. In FIG. 7, the fracture in the bone is first aligned, and then a K-wire is inserted into the bone. A K-wire or pin is known in the art and is a sterilized, smooth steel pin used in orthopedics and other types of medical applications. It is available in different sizes as needed and provides structure, support and in one version has a diameter of about 0.040".

In FIG. 7A a cannulated drill, using the K-wire as a guide, drills an opening into the metacarpal bone, wherein the opening extends through the fracture, or partially through the k wired construct, and provides enough space on each side of the fracture to properly position device 10.

In FIG. 7B, device 10 is rotatingly driven into the opening in the metacarpal bone using cannulated techniques. Second section 14 is first driven in, and then first section 12 is driven in. The width of second section 14 and first section 12 are both greater than the opening formed in the bone, so each section can thread into the opening. This provides bone material for the threads to grasp and retain device 10 in the opening.

Figure 7C:
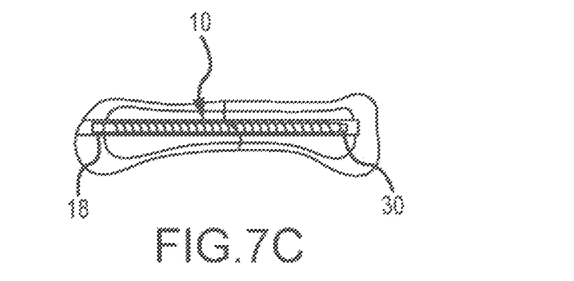
FIGS. 7C and 8 illustrate the device of FIGS. 1-6 positioned in a metacarpal bone.
Figure 8:
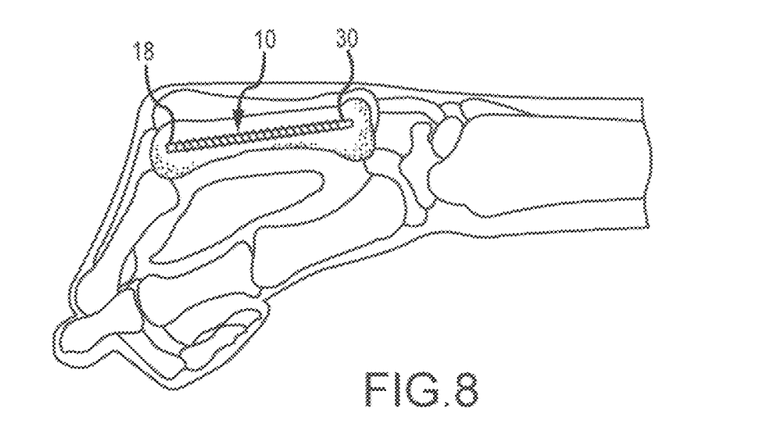

FIGS. 7C and 8 show device 10 in the metacarpal bone after the K-wire has been removed. Since device 10 is anchored in the metacarpal bone, there is no need for a second operation to remove it.

If a non-cannulated device is used, the Kwire may be used to form a pilot hole, and device 10 would be driven into the pilot hole.

In another aspect of the invention, the device has a single diameter with threads of the same pitch and height. This device may have a head similar to the one described above, but that is about 0.5 mm wider than the rest of the device, or about 7%-15% wider, in order to generate sufficient torque. Such a device may also have multiple self-tapping, or cutting structures, in order to reduce the amount of torque required to screw the device into an opening in a bone. For example, such a device may have one cutting structure at its distal tip, and one or more other cutting structures along its length, and/or a cutting structure juxtaposed the head so the head of the device does not extend beyond the bone.

Specific exemplary embodiments of the invention are described below:

1. A device for repairing a bone, the device for being received in the bone and comprising:
   (a) a shaft having a length and an outer surface,
   (b) a first end and a second end;
   (c) threads on the outer surface, wherein the threads comprise 85% or more of the shaft length; and
   (d) a driving surface at the first end;
   wherein the first section has a larger diameter than the second section of the device.

2. The device of example 1 wherein the device is comprised of one or more of nitinol, stainless steel and titanium steel.

3. The device of example 1 or 2, wherein the first section has a self-tapping configuration and the second section has a self-tapping portion.

4. The device of any of examples 1-3 wherein the first end has a diameter at least 7% wider than the diameter of the second end.

5. The device of any of examples 1-4 wherein the first end has a diameter that is 7%-15% wider than the diameter of the second end.

6. The device of any of examples 1-5 that has that has a length of between 3.5 cm and 8.5 cm, or 3.5 to 7.5 cm, or 4.0 to 8.0 cm, or about 7 cm.
7. The device of any of examples 1-6 wherein the first diameter is between 3.5 mm and 5.0 mm.
8. The device of any of examples 1-7 wherein the second diameter is between 3.0 mm and 4.5 mm.
9. The device of any of examples 1-8 that further includes a cutting surface at the second end.
10. The device of any of examples 1-9 that further includes a cutting surface between the first end and the second end.
11. The device of any of examples 1-10 that includes a cannula.
12. The device of any of examples 1-11 wherein the first end is between 0.3 mm and 0.7 mm greater in diameter than the diameter of the second end.
13. The device of any of examples 1-12 wherein the first end is between 7% and 15% greater in diameter than the diameter of the second end.
14. The device of any of examples 1-13 wherein the threads on the first end have the same pitch as a pitch of the threads on the second end.
15. The device of any of examples 1-13 wherein the threads on the first end have a different pitch than a pitch of the threads on the second end.
16. The device of any of examples 1-15 wherein the threads are continuous along the length of the device.
17. The device of any of examples 1-16 wherein the threads on the first section comprise up to 40% of the length of the device.
18. The device of any of examples 1-17 wherein the driving head is selected from the group consisting of designs that can accept one of the following drivers: a flat screwdriver, a Phillips screw driver, a hex head, and an Allen wrench.
19. The device of any of examples 1-8 wherein the driving head has the same diameter as the first end.
20. The device of any of examples 1-19 wherein the threads have the same height.
21. The device of any of examples 1-20 wherein the threads have the same height and pitch.
22. The device of any of examples 1-21 that has a length and the diameter of the first section is at least 4%, or at least 5%, of the length.
23. The device of any of examples 1-21 that has a length and the diameter of the first section is between 4% and 7% of the length.
24. The device of any of examples 1-21 that has a length and the diameter of the first section is between 4% and 10% of the length.

Having thus described some embodiments of the invention, other variations and embodiments that do not depart from the spirit of the invention will become apparent to those skilled in the art. The scope of the present invention is thus not limited to any particular embodiment, but is instead set forth in the appended claims and the legal equivalents thereof. Unless expressly stated in the written description or claims, the steps of any method recited in the claims may be performed in any order capable of yielding the desired result.

What is claimed is:

1. An orthopedic stabilization device having a total length, x, along a longitudinal axis and comprising:
   an external thread which extends along the entire total length, x, of the device;
   a first section having:
      a length, $l_1$, along the longitudinal axis, wherein $l_1$ forms 25-45% of the total length, x, and
      a major diameter, $d_1$, and a minor diameter, $d_2$,
      a first free end of the device, the first free end including a head configured to interface with a driver;
      a second end; and
      a transition portion that extends from the second end toward the first end of the first section, the transition portion including a cutting structure and a taper,
      wherein $d_1$ is substantially uniform between the first end and the transition portion of the first section; and
   a second section extending from the second end of the first section to a second free end of the device, the second section having:
      a length, $l_2$, along the longitudinal axis, wherein $l_2$ forms 55-75% of the total length, x, and
      a major diameter, $d_3$ extending from the second end of the first section, and a minor diameter, $d_4$, wherein $d_3$ is substantially uniform and the largest outer diameter of the second section, and
   wherein $d_1$ is 7-15% greater than $d_3$, and $d_2$ is greater than $d_4$.
2. The device of claim 1, wherein the device is comprised of one or more of nitinol, stainless steel, or titanium steel.
3. The device of claim 1, wherein the length, x, is between 3.5 cm and 8.5 cm.
4. The device of claim 1, wherein $d_1$ is between 3.0 mm and 4.5 mm.
5. The device of claim 1, wherein $d_3$ is between 3.0 mm and 4.5 mm.
6. The device of claim 1, wherein the second section has an end that includes a second cutting surface.
7. The device of claim 1, wherein the device includes a cannulation.
8. The device of claim 1, wherein $d_1$ is between 0.33 mm and 0.7 mm greater than the $d_3$.
9. The device of claim 1, wherein the external thread comprises one or more threads with a first pitch in the first section, and one or more threads with a second pitch in the second section, wherein the first pitch is the same as the second pitch.
10. The device of claim 1, wherein the external thread is a single thread along the length of the device.
11. The device of claim 1, wherein the first section comprises about 40% of the length, x, of the device.
12. The device of claim 1, wherein $d_1$ is at least 5% of the length, x.
13. The device of claim 1, wherein $d_1$ is between 4% and 7% of the length, x.
14. The device of claim 1, wherein $d_1$ is between 4% and 10% of the length, x.
15. The device of claim 1, wherein the external thread has a pitch of about 1 mm/revolution.
16. The device of claim 1, wherein the head has a minor diameter that is the same as $d_2$.
17. The device of claim 1, wherein a free end of the second section comprises a plurality of prongs that are offset from the longitudinal axis of the device.
18. An intramedullary fracture fixation device having a length, x, along a longitudinal axis and comprising:
   a thread extending along the entire length of the device, the thread having a constant pitch;
   a first section having a first length along the longitudinal axis, the first section comprising:
      a first, free end including a head configured to interface with a driver,
      a second end, a first portion having a first substantially uniform outer diameter extending from the first, free end of the first section; and a second portion extending from the first portion to the second end of the first section, wherein the second portion comprises a taper and a first cutting flute that includes one or more interruptions in the thread to form one or more serration;

a second section comprising:

a first end extending from the second end of the first section, a second, free end, wherein a tip at the second, free end of the second section comprises a second cutting flute, a second length along the longitudinal axis, and a second substantially uniform outer diameter that is smaller than the first substantially uniform outer diameter, and a cannulation extending through the length of the device, wherein an outer diameter of the taper of the second portion decreases from the first outer diameter at a first end of the taper to the second outer diameter at a second end of the taper, wherein the first end of the taper is further away from the second section than the second end of the taper.

* * * * *

UNITED STATES PATENT AND TRADEMARK OFFICE
CERTIFICATE OF CORRECTION

| | |
|---|---|
| PATENT NO. | : 11,147,604 B2 |
| APPLICATION NO. | : 14/993972 |
| DATED | : October 19, 2021 |
| INVENTOR(S) | : Lloyd P. Champagne et al. |

It is certified that error appears in the above-identified patent and that said Letters Patent is hereby corrected as shown below:

In the Specification

In Column 1, at Line 27, delete "cartilage" and insert --cartilage.--.

In Column 3, at Line 66, delete "may be have" and insert --may have--.

In Column 4, at Line 16, delete "k wired" and insert --K-wired--.

In the Claims

In Column 6, at approximately Line 34, in Claim 8, delete "0.33" and insert --0.3--.

Signed and Sealed this
Nineteenth Day of April, 2022

*Katherine Kelly Vidal*

Katherine Kelly Vidal
*Director of the United States Patent and Trademark Office*